US011021739B2

(12) United States Patent
Di Oto et al.

(10) Patent No.: US 11,021,739 B2
(45) Date of Patent: Jun. 1, 2021

(54) ADDITIVE FOR ACCELERATING HYBRIDIZATION

(71) Applicant: ALMA MATER STUDIORUM UNIVERSITA DI BOLOGNA, Bologna (IT)

(72) Inventors: Enrico Di Oto, San Lazzaro di Savena (IT); Valentina Monti, Modena (IT); Sofia Asioli, Bologna (IT)

(73) Assignee: ALMA MATER STUDIORUM UNEVERSETA DI BOLOGNA, Bologna (IT)

( * ) Notice: Subject to any disclaimer, the term of this patent is extended or adjusted under 35 U.S.C. 154(b) by 0 days.

(21) Appl. No.: 15/549,065

(22) PCT Filed: Feb. 3, 2016

(86) PCT No.: PCT/IB2016/050548
§ 371 (c)(1),
(2) Date: Aug. 4, 2017

(87) PCT Pub. No.: WO2016/125091
PCT Pub. Date: Aug. 11, 2016

(65) Prior Publication Data
US 2018/0023126 A1   Jan. 25, 2018

(30) Foreign Application Priority Data
Feb. 4, 2015   (IT) .......................... RM2015A000048

(51) Int. Cl.
*C12Q 1/6832* (2018.01)
*C12Q 1/6841* (2018.01)

(52) U.S. Cl.
CPC ......... *C12Q 1/6832* (2013.01); *C12Q 1/6841* (2013.01); *C12Q 2527/125* (2013.01)

(58) Field of Classification Search
CPC ............... C12Q 1/6832; C12Q 1/6841; C12Q 2527/125
See application file for complete search history.

(56) References Cited

U.S. PATENT DOCUMENTS

| | | | | |
|---|---|---|---|---|
| 4,743,554 A | * | 5/1988 | Boothroyd | C07K 14/005 424/186.1 |
| 5,206,344 A | * | 4/1993 | Katre | A61K 38/2013 424/278.1 |
| 5,789,167 A | * | 8/1998 | Konrad | C12Q 1/68 435/6.11 |
| 6,287,854 B1 | * | 9/2001 | Spurr | C07K 14/47 424/280.1 |
| 9,303,287 B2 | | 4/2016 | Matthiesen | |
| 2007/0010432 A1 | * | 1/2007 | Workman | C12Q 1/42 514/21.2 |
| 2011/0136764 A1 | * | 6/2011 | Appari | A61K 31/497 514/81 |
| 2011/0257176 A1 | * | 10/2011 | Villoutreix | A61K 31/41 514/236.2 |
| 2011/0311974 A1 | * | 12/2011 | Matthiesen | C12Q 1/6832 435/6.11 |
| 2011/0318745 A1 | * | 12/2011 | Matthiesen | C12Q 1/6832 435/6.11 |
| 2014/0242589 A1 | | 8/2014 | Matthiesen | |

OTHER PUBLICATIONS

PanReac AppliChem. Retrieved on Apr. 16, 2020 from: https://sds.chemicalsafety.com. (Year: 2020).*
Metzger et al. Journal of The Electrochemical Society. 2016. 163(7):A1219-A1225. (Year: 2016).*
Aslund, International Search Report and Written Opinion, dated May 24, 2016, PCT/IB2016/050548.

* cited by examiner

*Primary Examiner* — Joseph G. Dauner
(74) *Attorney, Agent, or Firm* — Greer, Burns & Crain, Ltd; Gregory P. Einhorn (57) ABSTRACT

The present invention describes an additive for accelerating hybridization comprising: a) an aqueous solution of sodium dextran sulphate, b) a salt, c) a buffer system, d) a strong mineral base possibly mixed with at least one polar aprotic solvent, or at least one polar aprotic solvent.
The additive described herein enables a reduction in the time required to perform the investigations with molecular probes on histological and cytological samples; the possibility of applying it to the protocol already in use in the routine practices of various laboratories in order to reduce the working time of histological and cytological samples for investigations with molecular probes, with no organisational impacts on the operators' work, enabling a more rapid diagnostic response for the patient and offering the possibility of using the additive described herein without formamide.

9 Claims, 1 Drawing Sheet

FIG. 1

ADDITIVE FOR ACCELERATING HYBRIDIZATION

This application is a national phase application claiming benefit of priority under 35 U.S.C. § 371 to International (PCT) Patent Application serial number PCT/162016/050548, filed Feb. 3, 2016, which claims benefit of priority to Italian Patent Application No RM2015A000048, filed Feb. 4, 2015. The aforementioned applications are expressly incorporated herein by reference in their entirety and for all purposes.

This invention relates to compounds and methods for the hybridization of molecular probes in the biotechnology and diagnostics sector. In particular, this invention concerns aqueous solutions, to be used as an accelerating adjuvant additive in the denaturation reaction and hybridization reaction of one or more molecular probes (for example DNA, RNA and PNA probes), even simultaneously, with targeted nucleic acids (DNA and/or RNA) on histological and/or cytological samples.

This invention concerns the field of molecular analysis of alterations by DNA and/or RNA by means of In-Situ Hybridization (ISH) techniques, both in the research and diagnostics field.

This invention also concerns a method for hybridization between the nucleic acids of the sample in question and the molecular probes.

BACKGROUND OF THE INVENTION

Within the field of molecular analysis techniques currently used in oncology, Fluorescence (FISH) and Non-fluorescence (SISH, CISH) In-Situ Hybridization (ISH) is widely applied to define the structure of diagnostic/prognostic/predictive markers.

Among the various methods, FISH represents the "gold standard" for sensitivity and specificity but usually requires an average working time of around 2-3 days. This is a burden on the management of an analysis laboratory but also a drawback for a patient waiting for the result of the analysis. Furthermore, the response time may be critical for starting the appropriate treatment, particularly in the case of personalised treatment. For a description of the In Situ Hybridization technique, refer to WO2009020932 and the references mentioned therein. See also Graziano F, Galluccio N, Lorenzini P, Ruzzo A, Canestrari E, D'Emidio S, Catalano V, Sisti V, Ligorio C, Andreoni F, Rulli E, Di Oto E, Fiorentini G, Zingaretti C, De Nictolis M, Cappuzzo F, Magnani M, "Genetic activation of the MET pathway and prognosis of patients with high-risk, radically resected gastric cancer". J. Clin. Oncol. vol 29, no. 36, pp. 4789-95, 2011.

Over time, other methods and commercial kits have been proposed as an alternative to the standard method. However, there are still limits imposed either by the high cost of the reagents or by the limited number of molecular probes compatible with the system, as well as the type of signal emitted by the molecular probe, necessary to see it, not always compatible with the existing microscope systems in the laboratories.

The buffers most commonly used in in-situ hybridization are, for example, composed of solvents, accelerating agents, blocking agents, salts, chelating agents and buffers. The most commonly used solvent is formamide in variable concentration of between 5% and 50%, the accelerating agent is for example sodium dextran sulphate in variable concentration of between 5% and 30% and the salts are represented, for example, by sodium chloride, sodium citrate and anhydrous tribasic sodium citrate.

In conventional buffers, blocking agents such as salmon sperm and chlelating agents such as EDTA may also be present.

Alternative proposals to the standard method are described in Matthiesen and Hansen, "Fast and non-toxic In-Situ Hybridization without Blocking of Repetitive Sequences" WO2009/144581, WO2010/097655, WO2010/097656, WO2010/097707 and WO2013/057310 and the references contained therein.

These limits exist, for example, in the IQFISH DAKO™ Kit which, although offering a reduction in the time taken to perform the FISH method, is very expensive and linked to just one molecular target (Her-2 gene and relative centromere test, using a probe stained with Texas Red).

A second aspect of the conventional methods to be evaluated is the presence of deionised formamide in the hybridization buffer. This compound is toxic to humans, its handling requires special precautions and there are strict rules on its disposal.

The present invention proposes to overcome the above-mentioned problems, in particular to reduce the analysis times and substantially reduce the use of formamide.

The present invention has further advantages, such as the low cost of the necessary reagents and the possibility to apply the method and the accelerating adjuvant accelerator proposed herein to any type of molecular probe, target tissue and staining.

The use of the present invention both in the research laboratory and in human diagnostics provides the clinician with a rapid response and improves the quality of life of the patient and the health services provided.

SUMMARY OF THE INVENTION

It has surprisingly now been discovered that by adding an aqueous saline solution that comprises sodium dextran sulphate, a strong mineral base possibly mixed with at least one polar aprotic solvent, or at least one polar aprotic solvent, to a molecular probe (in solution and/or in their commercial and/or production format) directly onto the sample to be examined, various advantages are obtained, including: a reduction in the time required to perform the investigations with molecular probes on histological and cytological samples; the creation of a fast, low-cost method for the hybridization of histological and cytological samples with molecular probes, with the possibility of applying it to the protocol already in use in the routine practices of various laboratories in order to reduce the working time of histological and cytological samples for investigations with molecular probes, with no organisational impacts on the operators' work; the possibility of applying the hybridization additive according to the present invention to the probes already in use in the routine practices of various laboratories without the need for increased expenditure on instrumentation or parts thereof; the possibility of repeating in one day any investigations with molecular probes on histological and cytological samples found to be inconclusive after applying the standard method and/or that proposed in the present invention; the possibility of using the additive described herein without formamide and thus with a lower level of toxicity; the possibility of performing that described above also on histological samples considered, due to particular biological and/or tissue characteristics and/or characteristics conferred by pre-analytical procedures, to be difficult to process.

The additive according to the present invention does not replace those already present when packaging or preparing molecular probes but is added as an accelerating adjuvant additive enabling the phases of denaturation and hybridization to be implemented.

The additive and method of hybridization that it uses according to the present invention can be applied to any system and/or model and/or biological sample, particularly for samples of human origin.

The present invention is suitable to be applied to any in-situ hybridization technique, preferably Fluorescence In-Situ Hybridization (FISH).

The additive and relative method of hybridization according to the present invention can be applied to any molecular system capable of hybridizing target nucleic acids on histological and/or cytological samples by means of complementary pairing of bases, for example DNA, RNA and suchlike.

The present invention also enables the quantity of molecular probe required for the success of hybridization to be reduced.

Consequently, an aim of the present invention is to provide an additive for accelerating hybridization comprising:
  a) an aqueous solution of sodium dextran sulphate,
  b) a salt,
  c) a buffer system,
  d) a strong mineral base possibly mixed with at least one polar aprotic solvent, or at least one polar aprotic solvent.

In an embodiment of the present invention, in said additive, said mineral base is a hydroxide of a metal. Preferably, said metal hydroxide is chosen from the group composed of sodium hydroxide, lithium hydroxide, potassium hydroxide, rubidium hydroxide, caesium hydroxide, beryllium hydroxide, magnesium hydroxide, calcium hydroxide, strontium hydroxide, barium hydroxide, aluminium hydroxide, gallium hydroxide, indium hydroxide and tin hydroxide. More preferably, said metal hydroxide is sodium hydroxide.

In an embodiment of the present invention, in said additive, said polar aprotic solvent is an organic solvent having a dipole moment of at least approximately 2 Debye units, a solubility in water of at least approximately 5% by volume at around room temperature and that does not undergo significant hydrogen exchange at around neutral pH. Preferably, said solvent is chosen from the group composed of ethylene carbonate, γ-butyrolactone, tetramethylene sulfone sulphur dioxide, acetonitrile, glycol sulphite/ethylene sulphite, propylene carbonate, ethylene trithiocarbonate, ε-caprolactone, N-methyl pyrrolidinone, acetanilide, N-acetylpyrrolidone, 4-amminopyridine, benzamide, benzimidazole, 1,2,3-benzotriazole, butadiene dioxide, 2,3-butylene carbonate, caprolactone, chloromaleic anhydride, 2-chlorocyclohexanone, chloronitromethane, citraconic anhydride, crotonolactone, cyclopropylnitrile, dimethyl sulphate, dimethyl sulfone, dimethyl sulfoxide, 1,2-dinitrobenzene, 2,4-dinitrotoluene, diphenyl sulfone, ethanesulfonyl chloride, furanic aldehyde, 2-furonitryl, isoxazole, maleic anhydride, malononitrile, 4-methyoxybenzonitrile, 1-methoxy-2-nitrobenzene, 1-methylimidazole, 3-methylisoxazole, N-methylmorpholine-N-oxide, methyl phenyl sulfone, methyl sulfolane, methyl-4-toluene sulfate, 3-nitroaniline, 2-nitrothiophene, 9,10-phenanthrenequinone, phthalic anhydride, 1,3-propane sultone, beta-propiolactone, 2-pyrrolidone, succinonitrile, sulfanilamide, 2,2,6,6-tetrachloro cylcohexanone, thiazole, 3,3,3-trichloropropene, 1,1,2-trichloropropene and 1,2,3-trichloropropene. More preferably said solvent is ethylene carbonate.

In an embodiment of the present invention, in said additive, said component d) is composed of an aprotic polar solvent.

In an embodiment of the present invention, said hybridization is in situ, in particular said hybridization is chosen from the group that consists of fluorescence hybridization and non-fluorescence hybridization.

In an embodiment of the present invention, said additive is used in determining the genetic constitution of Her2 in breast and gastric cancer in order to assign targeted therapy, or in determining ALK rearrangement in particular in lung and thyroid cancer in order to assign targeted therapy, or in determining a potential gene and chromosome alteration for diagnostic use, in particular in evaluating 1p36 and 19q13 chromosome deletions as prognostic factors, particularly in glial neoplasms, or in the determination of the gain of the gene TERC (3q26) as diagnostic/prognostic marker in potentially malignant lesions of the oral cavity (oral premalignant lesions, or OPML).

In an embodiment of the present invention, said additive is used for reprocessing samples that underwent hybridization, particularly in situ hybridization.

Another aim of the present invention is a method for the hybridization of molecular probes involving the use of the above-mentioned additive. In an embodiment of the present invention said additive is mixed with the molecular probe, preferably on the biological sample. In particular, said hybridization is in situ, for example chosen from the group that consists of FISH, CISH and SISH.

In an embodiment of the present invention, in said method, deparaffinization is performed hot.

The present invention will now be described in detail also by means of examples and figures.

DETAILED DESCRIPTION OF THE INVENTION

Definitions

In the context of the present invention, the following definitions shall apply.

A "biological sample" means any in vivo, in vitro or in situ sample formed by one or more cells or fragments of cells. This can, for example, be a single-cell or multi-cell organism, section of tissue, cytological sample, chromosome precipitate, sequences of purified nucleic acid sequences, artificial nucleic acid sequences, for example, based on a biological system or by chemical synthesis, microarray or other form of nucleic acid chip. In the embodiments mentioned, a sample means a mammal tissue sample such as, for example, human, feline or canine.

This definition also includes "histological and cytological samples".

"Nucleic acid", "nucleic acid chain" and "nucleic acid sequence" mean anything that binds to or hybridizes with a base pairing including, oligomers or polymers that have a structure formed by natural nucleotides and/or suchlike of nucleic acids comprising non-standard nitrogenous bases and/or non-standard structures (for example, a peptide nucleic acid (PNA) or locked nucleic acid (LNA)), or any derivatized form of a nucleic acid.

A "polar aprotic solvent" means an organic solvent having a dipole moment of around 2 or more Debye units, a solubility in water of at least around 5% (by volume) corresponding to or close to room temperature, namely around 20° C., and that does not undergo significant hydrogen exchange at around neutral pH, namely in the range between 5 and 9, in particular in the range of 6 to 8.

"Aqueous solution" means a solution containing water, even small amounts of water. For example, a solution containing 1% of water shall be deemed to be an aqueous solution.

"Hybridization" is deemed to include both the denaturation and hybridization phases of the hybridization procedure unless stated otherwise.

"Hybridization additive" or "hybridization solution" or "hybridization buffer, hereinafter even simply "additive", is deemed to be an aqueous solution necessary to implement the hybridization procedure, for example, to bind a molecular probe to a nucleic acid sequence of the sample.

Choice of Solvent and Strong Mineral Base

The additive according to the present invention comprises or may comprise at least one aprotic polar solvent.

As seen in the definitions given above, a polar aprotic solvent is an organic solvent having certain characteristics and performing the function of denaturant in the hybridization phase.

According to the present invention, said solvent may be present together with the strong mineral base or on its own.

Examples of aprotic polar solvent suitable for the present invention are ethylene carbonate (EC), γ-butyrolactone (GBL), sulfolane (SL), tetramethylene sulphur dioxide, acetonitrile (AN), glycol sulphite/ethylene sulphite (GS), propylene carbonate (PC), ethylene trithiocarbonate (ETC), ε-caprolactone; N-methyl pyrrolidinone, acetanilide, N-acetylpyrrolidone, 4-amminopyridine, benzamide, benzimidazole, 1,2,3-benzotriazole, butadiene dioxide, 2,3-butylene carbonate, caprolactone, chloromaleic anhydride, 2-chlorocyclohexanone, chloronitromethane, citraconic anhydride, crotonolactone, cyclopropylnitrile, dimethyl sulphate, dimethyl sulfone, dimethyl sulfoxide, 1,2-dinitrobenzene, 2,4-dinitrotoluene, diphenyl sulfone, ethanesulfonyl chloride, furanic aldehyde, 2-furonitryl, isoxazole, maleic anhydride, malononitrile, 4-methyoxybenzonitrile, 1-methoxy-2-nitrobenzene, 1-methylimidazole, 3-methylisoxazole, N-methylmorpholine-N-oxide, methyl phenyl sulfone, methyl sulfolane, methyl-4-toluene sulphate, 3-nitroaniline, 2-nitrothiophene, 9,10-phenanthrenequinone, phthalic anhydride, 1,3-propane sultone, beta-propiolactone, 2-pyrrolidone, succinonitrile, sulfanilamide, 2,2,6,6-tetrachloro cylcohexanone, thiazole, 3,3,3-trichloropropene, 1,1,2-trichloropropene and 1,2,3-trichloropropene.

The accelerating adjuvant additive according to the present invention is not a substitute for the buffer in which the molecular probes are packed, but is added to the commercial product, by means of hybridization with the target nucleic acids.

The additive of the present invention does not contain nucleic acids, chelating agents or blocking agents.

Optimization for Particular Applications

The accelerating adjuvant additive and relative method of hybridization according to the present invention may be modified in relation to particular application requirements whether in relation to the biological sample to be analysed (for example cytological, histological, etc.), to the system and/or model and/or biological sample (for example, insects, mouse, cat, dog, etc.) or to the molecular probes used.

For example, it is possible to vary the times relating to the thermal and enzymatic treatments in relation to the pre-analytical processing of the biological sample in question.

For example, it is possible to vary the concentrations of the various components of the accelerating adjuvant additive in relation to the characteristics of the biological sample in question and/or of the molecular probe used.

For example, it is possible to vary the co-denaturation temperature of the molecular probe in use with the target nucleic acid in relation to the specifications of the instructions of the probe's manufacturer.

For example, it is possible to vary the post co-denaturation hybridization temperature of the molecular probe in use with the target nucleic acid in relation to the specifications of the instructions of the probe's manufacturer.

Applications, Methods and Uses

Another aim of the present invention is a method for the hybridization of molecular probes that involves the use of the above-described additive.

In a preferred embodiment of the invention, said hybridization is in situ and in particular said hybridization is chosen from the group that consists of FISH, CISH and SISH.

Figure 1:
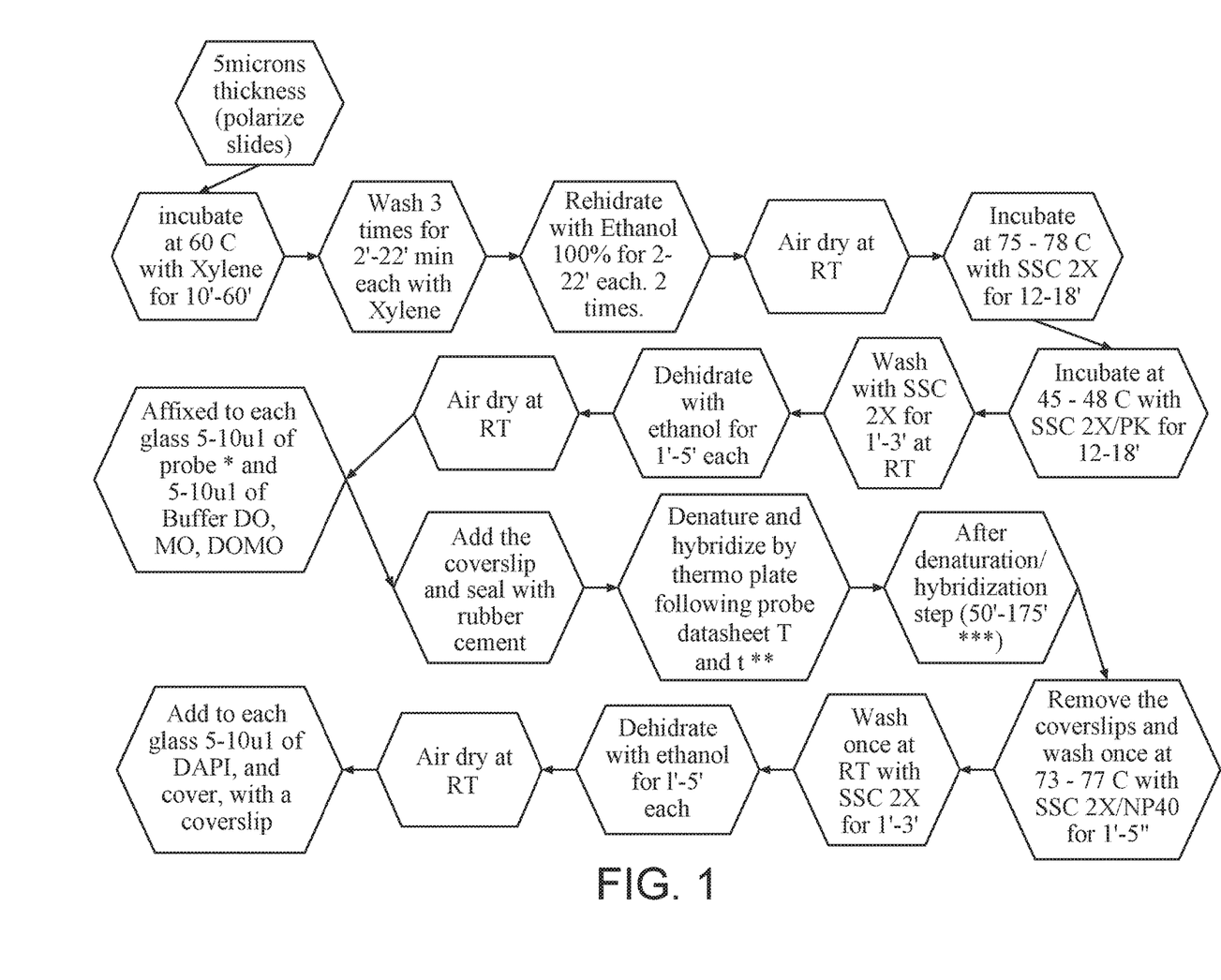
FIG. 1 shows a flow diagram of an embodiment of the method according to the present invention.

Referring to an embodiment in FIG. 1, said method involves:
  incubation of the biological sample in a drying oven, for example at a temperature of 60° C.;
  incubation in immersion in a solution containing a diaphonization agent, such as limonene, in a drying oven, for example at a temperature of 60° C.;
  incubation in immersion in an aqueous solution based on sodium chloride, anhydrous tribasic sodium citrate, for example at a temperature of 77° C., for example in a thermostatically-controlled bath;
  incubation in immersion in an aqueous solution based on sodium chloride, anhydrous tribasic sodium citrate, supplemented with an enzymatic protein capable of digesting the peptide bonds of the cellular proteins such as, for example, proteinase K, for example at a temperature of 47° C., for example in a thermostatically-controlled bath.

The steps described thus far are performed using conventional methods and reagents.

The hybridization method according to the present invention envisages the following phases for the hybridization phase of the nucleic acids of the sample with the molecular probe:
  attaching a suitable quantity of the molecular probe used, in its commercial formulation, to the previously prepared sample;
  attaching a suitable quantity of the accelerating adjuvant additive according to the present invention to the sample referred to in the previous point;
  mixing the quantity of molecular probe used, in its commercial formulation, attached to the sample with the quantity of accelerating adjuvant additive buffer according to the present invention, directly onto the sample;
  attaching a coverslip and sealing it with vinyl adhesive or similar, such as RUBBER CEMENT™;
  placing the samples prepared as described in the preceding points on a TOPBRITE™ type heated plate at the specific temperature for each probe as per the manufacturer's instructions (for example 75° C.) for the minimum time necessary for the correct denaturation of the nuclei acids (for example 15 minutes);
  cooling the samples whilst still on the heated plate referred to in the preceding point until the optimum hybridization temperature is reached;

incubating for the hybridization phase, whilst still on the above-mentioned heated plate, at the optimum temperature as per the manufacturer's instructions (for example 37° C.) for a shorter time than the standard method (for example 40 minutes with the method according to the present invention as against the overnight period of the conventional method). In order to check that hybridization has taken place and to determine the optimum temperature, the slides are removed from the hybridization plate, the subsequent stringency and nuclear contrast processes are performed and the slides are observed under the microscope, comparing them with the sample processed using the standard method. Of course, the method can later be standardised on the basis of the experiment and the type of sample examined.

The hybridization method according to the present invention also envisages using heat treatments of the histological and cytological samples for the post-hybridization phase of the nucleic acids of the sample with the molecular probe, comprising:

incubation in immersion in an aqueous solution based on sodium chloride, anhydrous tribasic sodium citrate and NP40 (octylphenoxypolyethoxyethanol), for example at a temperature of 75° C., for example in a thermostatically-controlled bath.

The hybridization method according to the present invention envisages, in order to view the preparation under the fluorescence microscope during the post-hybridization phase of the nucleic acids of the sample with the molecular probe:

attaching a suitable quantity of a solution containing DAPI (2-(4-amidino phenyl)-1H-indole-6-carboxamidine) to which PPD (1,4-diaminobenzene) may or may not be added to prevent the loss of the fluorescent signal due to exposure to light sources (photobleaching);
attaching a coverslip.

It is understood that any variations to the above-described method that are common general knowledge within the sector, for example variations of heat treatments, reagents and conditions, fall within the scope of the present invention, characterised by the use of the above-described hybridization additive.

The accelerating adjuvant additive according to the present invention allows hybridization in situ analysis, for example FISH, to be performed in a very short time, for example reduced to 157-165 minutes compared to around 210 minutes of the fastest system currently available on the market.

The accelerating adjuvant additive and the relative method of hybridization according to the present invention can be used as they are, or partly modified. For example, it is possible to make the appropriate adaptations depending on the biological sample to be treated, and to adapt it to that already used in the laboratory by changing the treatment and deparaffinization times for example in all of the hybridizations in situ that relate to the fields of cytology, histology and molecular biology, in the human, animal, plant and microbiological context.

The accelerating adjuvant additive and relative method of hybridization according to the present invention can also be used in association with standard methods possibly modified to suit operational requirements.

In a preferred embodiment of the present invention, said additive is used in a hybridization method to determine the genetic constitution of Her2 in breast and gastric cancer in order to assign targeted therapy.

In a preferred embodiment of the present invention, said additive is used in a method of hybridization to determine the ALK rearrangement in particular in lung and thyroid cancer in order to assign a targeted therapy.

In a preferred embodiment of the present invention, said additive is used in a method of hybridization to determine a potential gene and chromosome alteration, useful for diagnostic purposes.

In a preferred embodiment of the present invention, said additive is used in a method of hybridization to evaluate 1p36 and 19q13 chromosome deletions as prognostic factors, particularly in glial neoplasms.

In a preferred embodiment of the present invention, said additive is used in a method of hybridization for the evaluation of the gain of copies of the gene TERC (3q26) as diagnostic/prognostic marker in potentially malignant lesions of the oral cavity (oral premalignant lesions, or OPML).

The accelerating adjuvant additive and relative method of hybridization according to the present invention can also be used in the case of a second processing of the same sample if the first analysis is not technically conclusive.

In conventional hybridization protocols, FFPE samples must be stripped of paraffin by undergoing successive washes, typically in xylol for 10-20 minutes each, rehydrated usually in alcohols (3-5 washes of 2 to 5 minutes each) and subjected to thermal and protease treatments, for example in SSC2× at 75° C. for 1-20 minutes and SSC2×/Proteinase K at 45° C. for 1-20 minutes.

This is followed by a co-denaturation phase of the molecular probe used with the nucleic acids of the sample at a temperature stated in the instructions of the probe's manufacturer or set by the individual laboratory, for a time, for example, of 15 minutes.

Next comes the hybridization phase of the molecular probe used with the nucleic acids of the sample at a temperature stated in the instructions of the probe's manufacturer or set by the individual laboratory, for a time specified as "overnight".

After hybridization, the sample undergoes a stringency wash, for example in SSC2×/NP40 at 75° C. for 1-3 minutes, and is then dehydrated and mounted for analysis.

The method according to the present invention involves the following steps:

If the tissue is Formalin-Fixed and Paraffin-Embedded (FFPE), obtain 4-5 μm sections to be placed on a polarized slide.

In a thermostatically-controlled bath, set a temperature of 67° C.-100° C., preferably 70° C.-92° C., more preferably 71° C.-84° C. (optimum temperature 77° C.).

Insert a vertical tray containing 100 ml of citrate buffer at pH 7 (SSC2×, obtained by diluting a SSC20× stock solution comprising: 175.3 g of sodium chloride, 119.05 g of anhydrous tribasic sodium citrate and bi-distilled water to a final volume of 1 litre).

In a thermostatically-controlled bath, set a temperature of 33° C.-73° C., preferably 40° C.-63° C., more preferably 40° C.-53° C. (optimum temperature 47° C.).

Insert a vertical tray containing 100 ml of citrate buffer at pH 7 (SSC2×, obtained by diluting a SSC20× stock solution comprising: 175.3 g of sodium chloride, 119.05 g of anhydrous tribasic sodium citrate and bi-distilled water to a final volume of 1 litre).

In a thermostatically-controlled bath, set a temperature of 67° C.-100° C., preferably 66° C.-92° C., more preferably 66° C.-84° C. (optimum temperature 75° C.).

Insert a vertical tray containing 100 ml of citrate buffer at pH 7 (SSC2×, obtained by diluting a SSC20× stock solution comprising: sodium chloride 175.3 g, anhydrous tribasic sodium citrate 119.05 g and bi-distilled water to a final volume of 1 litre) in which has been diluted a suitable quantity of octylphenoxypolyethoxyethanol or similar non-ionic non-denaturing detergent, as a percentage of the total volume of between 0.1%-15%, preferably 0.3%-9% (optimum range 1.5%).

If necessary, gradually bring the molecular probes used to room temperature.

Bring the hybridization additive according to the present invention to room temperature in the composition suitable for the material to be analysed.

General composition of the accelerating adjuvant additive: the percentages are expressed in weight/volume in the case of a solid, or in volume/volume in the case of liquids.

Sodium hydroxide: as a percentage of the final volume between 0%-54%, preferably 0.3%-28%, more preferably 0.3%-14% (optimum concentration 1.07%).

Ethylene carbonate heated to a temperature of 37° C. as a percentage of the final volume between 0%-54%, preferably 10%-40%, more preferably 20%-35% (optimally 28.57%).

Sodium dextran sulphate (prepared by diluting 2.5 g of sodium dextran sulphate in 5 ml of bi-distilled water at 60° C.) as a percentage of the final volume between: 0.1%-55%, preferably 20%-50%, (optimally as regards the application of the buffer according to the present invention: 28.57% and 49.46%).

Bi-distilled water as a percentage of the final volume between: 0.1%-55%, preferably 10%-40% (optimally as regards the application of the buffer according to the present invention 28.57% and 32.97%).

Citrate buffer (also called SSC20×): sodium chloride 175.3 g, anhydrous tribasic sodium citrate 119.05 g, bi-distilled water to a final volume of 1 litre as a percentage of the final volume between: 0.1%-55%, preferably 10%-40%, more preferably 3%-25% (optimally as regards the application of the buffer according to the present invention 14.29% and 16.48%).

For cases deemed to be "standard" due to histological and/or pre-analytical processing characteristics and/or for the reprocessing of cases considered to be "difficult" due to histological and/or pre-analytical processing characteristics and/or inconclusive after an initial diagnosis using the standard method and/or all or part of that proposed in the present invention to use at room temperature, the accelerating adjuvant additive according to the present invention in the so-called "DO" formulation is comprised as follows:

Ethylene carbonate heated to a temperature 37° C. as a percentage of the final volume between the following intervals: 0.1%-54%, preferably 10%-40%, more preferably 20%-35% (optimally 28.57%).

Sodium dextran sulphate (prepared by diluting 2.5 g of sodium dextran sulphate in 5 ml of bi-distilled water at 60° C.) as a percentage of the final volume between: 0.1%-55%, preferably 10%-40%, more preferably 24%-35% (optimally 28.57%).

Bi-distilled water as a percentage of the final volume between: 0.1%-55%, preferably 10%-40%, more preferably 24%-35% (optimally 28.57%).

SSC20× comprising: sodium chloride 175.3 g, anhydrous tribasic sodium citrate 119.05 g, bi-distilled water to a final volume of 1 litre, as a percentage of the final volume between: 0.1%-55%, preferably 3%-40%, more preferably 10%-25% (optimally 14.29%).

For cases deemed to be "difficult" due to histological and/or pre-analytical processing characteristics and/or to the reprocessing of cases considered to be "standard" due to histological and/or pre-analytical processing characteristics and/or inconclusive after an initial diagnosis using the standard method and/or all or part of that proposed in the present invention to use at room temperature, the accelerating adjuvant additive according to the present invention in the so-called "MO" formulation is comprised as follows:

Sodium hydroxide as a percentage of the final volume between: 0%-54%, preferably 0.3%-28%, more preferably 0.3%-14% (optimally 1.07%).

Sodium dextran sulphate (prepared by diluting 2.5 g of sodium dextran sulphate in 5 ml of bi-distilled water at 60° C.) as a percentage of the final volume between: 0.1%-55%, preferably 25%-73%, more preferably 20%-50% (optimally 49.46%).

Bi-distilled water as a percentage of the final volume between: 0.1%-55%, preferably 25%-49%, more preferably 10%-40% (optimally 32.97%).

SSC20× comprising: sodium chloride 175.3 g, anhydrous tribasic sodium citrate 119.05 g, bi-distilled water to a final volume of 1 litre, as a percentage of the final volume between: 0.1%-55%, preferably 10%-40%, more preferably 7%-25% (optimally 16.48%).

For cases deemed to be "standard" due to histological and/or pre-analytical processing characteristics and/or for the reprocessing of cases considered to be "difficult" due to histological and/or pre-analytical processing characteristics and/or inconclusive after an initial diagnosis using the standard method and/or all or part of that proposed in the present invention and/or for treatments of cases deemed to be "standard" due to histological and/or pre-analytical processing characteristics and/or for treatments of cases deemed to be "difficult" due to histological and/or pre-analytical processing characteristics to use at room temperature, the accelerating adjuvant additive according to the present invention in the so-called "DOMO" formulation is comprised as follows:

Sodium hydroxide as a percentage of the final volume between: 0%-54%, preferably 0.1%-20%, more preferably 0.15%-12%, (optimally 0.43%).

Ethylene carbonate heated to a temperature of 37° C. as a percentage of the final volume between 0.1%-54%, preferably 10%-40%, more preferably 3%-35% (optimally 13.86%).

Sodium dextran sulphate (prepared by diluting 2.5 g of sodium dextran sulphate in 5 ml of bi-distilled water at 60° C.) as a percentage of the final volume of between: 0.1%-55%, preferably 10%-40%, more preferably 24%-35% (optimally 28.75%).

Bi-distilled water as a percentage of the final volume between: 0.1%-55%, preferably 24%-35%, more preferably 10%-40% (optimally 28.57%).

SSC20× comprising: sodium chloride 175.3 g, anhydrous tribasic sodium citrate 119.05 g, bi-distilled water to a final volume of 1 litre as a percentage of the final volume between: 0.1%-55%, preferably 10%-40%, more preferably 3%-25% (optimally 13.68%).

Heat to 37° C. an aliquot of Proteinase K (obtained by diluting the stock solution of Proteinease K with an appropriate quantity of bi-distilled water) with a volume between: 100 μl-2,000 μl, preferably 200 μl-1,500 μl, more preferably 300 μl-1,200 μl (optimally 625 μl) and a concentration between 0.05 mg/ml-1.11 mg/ml, preferably 0.15 mg/ml-0.82 mg/ml, more preferably 0.05 mg/ml-0.52 mg/ml (optimally 0.25 mg/ml).

Immerse the sections in xylol or (R) or (S)-limonene in the oven, at a temperature of between 33° C.-73° C., preferably 43° C.-67° C., more preferably 53° C.-63° C. (optimally 60° C.), for a time between: 5.2'-64', preferably 20'-49', more preferably 25'-35' (optimally 30').

Then perform 3 successive washes in xylol/limonene in a horizontal tray oscillating for a time for each one between: 1'-24', preferably 2'-10', more preferably 3'-9' (optimally 4').

Air dry at room temperature.

Then perform 2 successive washes in 100% ethanol in a horizontal tray oscillating for a time for each one between: 1'-24', preferably 2'-10', more preferably 3'-9' (optimally 4').

Air dry at room temperature.

Immerse the dried sections in the tray containing 100 ml of SSC2× at a temperature of between 67° C.-100° C., preferably 70° C.-92° C., more preferably 71° C.-84° C. (optimally 77° C.), for a time between: 1'-24', preferably 6'-18', more preferably 7'-23' (optimally 13' for breast and thyroid; 14' for lung; 20' for carcinoma of oral cavity).

After 1 to 3 minutes have elapsed, dissolve the Proteinase K in the tray containing 100 ml of SSC2× at a temperature of between: 33° C.-73° C., preferably, 40° C.-63° C., more preferably 43° C.-53° C., (optimally 47° C.).

After the remaining minutes have elapsed, immerse the sections in the tray containing 100 ml of SSC2× at a temperature of between: 33° C.-73° C., preferably 40° C.-63° C., more preferably 43° C.-53° C. (optimally 47° C.), for a time between: 1'-24', preferably 6'-18', more preferably 7'-23' (optimally 13' for breast and thyroid; 14' for lung; 20' for carcinoma of oral cavity).

Then wash the slides in 100 ml of SSC2× in a vertical tray for a time of between 30"-6', preferably 1'-5' (optimally 2').

Dehydrate the sections by washing them in progressively higher concentrations of alcohol:

for a time between: 30"-6', preferably 1'-5' (optimally 2') in a vertical tray containing 100 ml of 70% ethanol (obtained by diluting 70 ml of 100% ethanol with 30 ml of bi-distilled water) for a time between: 30"-6', preferably 1'-5' (optimally 2') in a vertical tray containing 100 ml of 85% ethanol (obtained by diluting 85 ml of 100% ethanol with 15 ml of bi-distilled water) for a time between: 30"-6', preferably 1'-5' (optimally 2') in a vertical tray containing 100 ml of 100% ethanol.

Air dry at room temperature.

At the same time, incubate at 37° C. an aliquot of the accelerating adjuvant additive according to the present invention in the composition suitable for the material to be analysed.

Attach to the sections a suitable quantity of molecular probe as per the preparation or commercial package, and add directly onto the section an equal quantity of the accelerating adjuvant additive buffer according to the present invention in the composition suitable for the material to be analysed.

Directly mix on the section the quantity of molecular probe dispensed with the same quantity of the accelerating adjuvant additive buffer according to the present invention in the composition suitable for the material to be analysed.

Fit a coverslip and seal with vinyl adhesive or similar, such as Rubber Cement™.

Incubate the section on a heated plate (hybridizer) according to the following schedule:

Denaturation phase with temperature and times according to the instructions of the molecular probe used.

Hybridization phase with temperature according to the instructions of the molecular probe used for a time between: 14'-160', preferably 25'-120', more preferably 11'-80' (optimally 40').

When the time has elapsed, remove the sealant by immersing the sections in a vertical tray containing 100 ml of SSC2× at room temperature.

Then immerse the sections in the tray containing 100 ml of SSC2×, (octylphenoxypolyethoxyethanol), as a percentage of the final volume between: 0.1%-15%, preferably 0.3%-9% (optimally 1.5%) at a temperature between: 67° C.-100° C., preferably 70° C.-92° C., more preferably 71° C.-84° C. (optimally 75° C.) for a time between: 30"-6', preferably 1'-5' (optimally 3').

Then wash the slides in 100 ml of SSC2× in a vertical tray for a time between 30"-6', preferably 1'-5' (optimally 2').

Dehydrate the sections by washing them in progressively higher concentrations of alcohol for a time between: 30"-6', preferably 1'-5' (optimally 2') in a vertical tray containing 100 ml of 70% ethanol for a time between: 30"-6', preferably 1'-5' (optimally 2') in a vertical tray containing 100 ml of 85% ethanol for a time between: 30"-6', preferably 1'-5' (optimally 2') in a vertical tray containing 100 ml of 100% ethanol.

Air dry at room temperature.

Attach to the sections a suitable quantity of DAPI (2-(4-amidinophenyl)-1H-indole-6-carboxamidine) to which may be added PPD (1,4-diaminobenzene) in order to prevent loss of the fluorescent signal due to exposure to light sources, i.e. photobleaching.

Then fit the coverslip.

Keep in the dark at +4° C. or proceed to the reading phase.

The average optimum total time from the start of the procedure is between 157 minutes and 165 minutes depending on the tissue analysed with the accelerating adjuvant additive according the present invention. For comparison, the average time of a conventional procedure is around 24 hours.

It has also been discovered, and it is another aspect of the present invention, that by conducting the preliminary hot-deparaffinization phase, at between around 30° C. and around 60° C., the total times of the procedure can be further reduced.

Therefore, the method according to the present invention reduces the overall working time thanks to the reduction in the deparaffinization and rehydration times (from around 1 hour to around 40 minutes) and, above all to the reduction in the plate-hybridization time of the probe with target nucleic acid (from overnight [o/n] to 40') due to the effect of the accelerating additive buffer.

The present invention will now be further illustrated by the following examples.

EXAMPLES

The reagents used in the following examples are:

Microcleaning (Xylene substitute, D-limonene Based) from the Diapath S.p.A. Company (X0025) to remove paraffin; Absolute Diawhite (colourless alcohol mixture with an absolute grade of 99.7-99.9%) from the Diapath S.p.A Company (A0165) for initial partial rehydration; distilled water from the Carlo Erba Company (307582) to prepare buffers and dilutions of alcohol; absolute ethyl alcohol from the Panreac Company (1091 PA) to progressively increase the alcohol concentrations for the dehydration phase; sodium chloride from the Carlo Erba Company (368259) for preparing the sodium citrate (SSC) buffer; anhydrous tribasic sodium citrate from the Carlo Erba Company (E368107) for preparing the sodium citrate buffer (SSC); NONINDET® P40 Substitute from the Fluka Company (31903213) for preparing the stringency buffer; sodium hydrate from the Carlo Erba Company (480507) for preparing the hybridization additive; ethylene carbonate from the Aldrich Company (E26258-500G) for preparing the hybridization additive; sodium dextran sulphate from the Sigma Company (42867-25G) for preparing the hybridization additive; Pepsin from porcine gastric mucosa from the Sigma Company (P7125-100G) for protease treatment of cytological samples; 10% neutral buffered formalin from the Bio-Optica Company (05-K01009) for preparing the post-fixation buffer of the cytological samples; magnesium chloride from the Sigma Company (M8266-1KG) for preparing the post-fixation buffer of the cytological samples; 37% hydrochloric acid from the Carlo Erba Company (7647-01-0) for preparing the protease treatment buffer of the cytological samples; Proteinase K, recombinant, PCR grade from the Roche Diagnostics Company (03 115 852 001) for the protease treatment of the Formalin-Fixed Paraffin-Embedded (FFPE) histological samples or cell-block cytological samples; mix of POSEIDON™ ERBB2, Her-2/neu (17q12)/SE 17 control probes from the Kreatech Diagnostics Company (KBI-10701) to assess the gene amplification of the Her-2 gene; mix of probes in the Vysis EGFR/CEP7 Fluorescence In-Situ Hybridization (FISH) Probe Kit from the Abbott Molecular Company (01N35-020) to assess the amplification of the EGFR gene and the aneusomy of chromosome 7; Mix of probes in the Vysis ALK BREAK APART FISH PROBE KIT™ from the Abbott Molecular Company (06N38-020) to assess the rearrangement of the ALK gene; Mix of probes in the Vysis 1p36/1q25 and 19q13/19p13 FISH Probe Kit from the Abbott Molecular Company (4N6020) to assess the 1p36 and 19q13 chromosome deletions; Mix of probes cervical cancer (3Q26, 8Q24, A-SAT CHR. 7) ditta Kreatech Diagnostics (KBI-10704) for the evaluation of the gain of the copies of the gene as diagnostic/prognostic marker in the potentially malignant lesions of the oral cavity (OPML); RUBBER CEMENT™ from the Royal Talens Company (95306500) to seal the coverslips during the denaturation/hybridization phase of the molecular probe with the nucleic acid of the sample; 4',6-diamidino-2-phenylindole (DAPI) Counterstain from the Kreatech Diagnostics Company (LK-096A) to counterstain the nuclei at the end of the method for performing hybridization in situ;

for the high-temperature deparaffinization stages the Digit-HOT drying oven of the PBI International Company (56297) was used; for the thermal and protease treatments, a Clifton two-well thermostatically-controlled bath and a thermostatically-controlled bath with oscillator from the Bicasa Company were used; for the denaturation and hybridization stages, a TopBrite heated plate from the Rosnova s.r.l. Company (TB-001S) was used.

The assessment of the FISH preparations was carried out within 3 days of hybridization, using a Nikon BX61 fluorescence microscope fitted with DAPI FITC, TRITC, B/G, and U/B/G filters and 4×, 20×, 40× and 100× immersion lenses.

Example 1—FISH Procedure on Histological and/or Cell-Block Samples

The sections of tissue (breast, lung, thyroid and brain) or FFPE cell-block material are cut to a thickness of 4-5 µm and placed under polarized slides.

They are then incubated in a drying oven for 30 minutes at 60° C. and deparaffinized for 30 min in xylol, also at 60° C.

The sections are then immersed in 3 successive washes of xylol at room temperature for 4 minutes each, under agitation.

Subsequently, the sections are air dried at room temperature and undergo 2 successive washes in 100% ethanol for 5 minutes each, under agitation.

The sections are then air dried at room temperature.

Once dried, the sections are transferred into the sodium citrate SSC2× buffer and heated to a temperature of 77° C. for the following times: breast and thyroid and relative neoplastic lesions 13 minutes, lung and relative neoplastic lesions 14 minutes, brain and relative neoplastic lesions 14 minutes.

The sections are then transferred into the sodium citrate SSC2× buffer, in which has been dissolved a 625 µl aliquot of Proteinase K 20 mg/ml and heated to 47° C. for the following times: breast and thyroid and relative neoplastic lesions 13 minutes, lung and relative neoplastic lesions 14 minutes, brain and relative neoplastic lesions 14 minutes.

The samples are then washed in SSC2× at room temperature for 2 minutes and dehydrated by washing them in progressively higher concentrations of alcohol (70%, 85%, 100%) for 2 minutes each.

They are then air dried at room temperature.

Once dried, attach to the sections 3-5 µl of a mix of specific probes (Her2/CEP17; EGFR/CEP7; ALK-EML4; 1p36/1q25; 19q13/19p13; 3Q26, 8Q24, A-SAT CHR. 7) and then add some of the accelerating adjuvant additive buffer according to the present invention, to be precise: DO for the breast samples and MO for the thyroid, lung, brain and oral samples.

Then re-suspend the mix of specific probes on the slide, together with the relative accelerating adjuvant additive of the present invention, fit a coverslip and seal with RUBBER CEMENT™.

Place the slides thus prepared on the TopBrite hybridization plate set to the following parameters:

Denaturation: 75° C. for 15'
Hybridization: 37° C. for 40'

Once the phase generally known as hybridization has been completed, the coverslip is removed by immersing the slides in a sodium citrate SSC2× buffer and subjecting them to a stringency wash in SSC2×-NP40 at 73° C. for 3 minutes in the case of breast, thyroid and relative neoplastic lesions and lung, brain and relative neoplastic lesions, oral cavity and relative neoplastic and pre-neoplastic lesions. The samples are then washed in SSC2× at room temperature for 2 minutes and dehydrated by washing them in progressively higher concentrations of alcohol (70%-85%-100%) for 2 minutes each.

They are then air dried at room temperature.

The procedure is concluded by mounting the sample with DAPI counterstain and fitting the coverslip.

Example 2—FISH Procedure on Cytological Samples

The coverslip is removed from the previously stained cytological samples.

The samples then undergo 3 xylol washes of 20 minutes each.

The sections are then air dried at room temperature and undergo 2 successive washes in 100% ethanol for 5 minutes each, under agitation.

The slides are then immersed in SSC2× at room temperature for 2 minutes and incubated in SSC2× at 73° C. for 2 minutes.

An enzymatic treatment in 0.01N HCl/Pepsin 0.5 g is then performed at 37° C. for 30 minutes.

The samples are then incubated in a buffered neutral 1% formalin/MgCl$_2$ solution for 5 minutes at room temperature.

The samples are then washed in SSC2× at room temperature for 2 minutes and dehydrated in progressively higher concentrations of alcohol (70%-85%-100%) for 2 minutes each.

They are then air dried at room temperature.

Once dried, attach to the sections 3-5 µl of a mix of specific probes (Her2/CEP17; EGFR/CEP7; ALK-EML4; 1p36/1q25; 19q13/19p13) and then add an aliquot of the accelerating adjuvant additive according to the present invention, to be precise: DO for the breast samples and MO for the thyroid and lung samples.

Then re-suspend on the slide the mix of specific probes with the accelerating adjuvant additive according to the present invention, fit the coverslip and seal with RUBBER CEMENT™.

Place the slides thus prepared on the TopBrite hybridization plate set to the following parameters:

Denaturation: 75° C. for 15'
Hybridization: 37° C. for 40'

Once the phase generally known as hybridization has been completed, the coverslip is removed by immersing the slides in a sodium citrate SSC2× buffer and subjecting them to a stringency wash in SSC2×-NP40 at 73° C. for 3 minutes in the case of breast, thyroid and relative neoplastic lesions; 2 minutes in the case of lung, brain and relative neoplastic lesions. The samples are then washed in SSC2× at room temperature for 2 minutes and dehydrated by washing them in progressively higher concentrations of alcohol (70%-85%-100%) for 2 minutes each.

They are then air dried at room temperature.

The procedure is concluded by mounting the sample with DAPI counterstain and fitting the coverslip.

Example 3—FISH Procedure for Reprocessing (Both for Histological and FFPE Cell-Block Samples and for Cytological Samples)

This applies to the reprocessing of cases deemed to be "standard" due to histological and/or pre-analytical processing characteristics and/or to the reprocessing of cases deemed to be "difficult" due to histological and/or pre-analytical processing characteristics and/or inconclusive after an initial diagnosis using the standard method and/or all or part of that proposed in the present invention.

Remove the coverslip by immersing the samples in SSC2×[1] at room temperature for 10 minutes, under agitation, dehydrate them by washing them in progressively higher concentrations of alcohol (70%-85%-100%) for 2 minutes each and air dry them at room temperature.

The sections are then immersed in 3 successive washes of xylol at room temperature for 10 minutes each, under agitation.

The sections are then air dried at room temperature and undergo 2 successive washes in 100% ethanol for 5 minutes each, under agitation.

The sections are then air dried at room temperature.

Once dried, the sections are transferred to the sodium citrate SSC2× buffer, heated to a temperature of 77° C. for a variable time depending on the cause of the failure of the first process (usually varying between 30 seconds and 3 minutes).

They are then transferred to the sodium citrate SSC2× buffer, in which has been dissolved a 625 µl aliquot of Proteinase K 20 mg/ml and which is heated to 47° C. for the following times: for a variable time depending on the cause of the failure of the first process (usually varying between 30 seconds and 3 minutes).

The samples are then washed in SSC2× at room temperature for 2 minutes and dehydrated by washing them in progressively higher concentrations of alcohol (70%, 85%, 100%) for 2 minutes each.

They are then air dried at room temperature.

Once dried, attach to the sections 3-5 µl of a mix of specific probes (Her2/CEP17; EGFR/CEP7; ALK-EML4; 1p36/1q25; 19q13/19p13; 3Q26, 8Q24, A-SAT CHR. 7) and then add an aliquot of the accelerating adjuvant additive according to the present invention, to be precise: DOMO.

Then re-suspend on the slide the mix of specific probes with the accelerating adjuvant additive according to the present invention, fit the coverslip and seal with RUBBER CEMENT™.

Place the slides thus prepared on the TopBrite hybridization plate set to the following parameters:

Denaturation: 75° C. for 15'
Hybridization: 37° C. for 40'

Once the phase generally known as hybridization has been completed, the coverslip is removed by immersing the slides in a sodium citrate SSC2× buffer and subjecting them to a stringency wash in SSC2×-NP40 at 73° C. for 3 minutes in the case of breast, thyroid and relative neoplastic lesions and lung, brain and relative neoplastic lesions. The samples are then washed in SSC2× at room temperature for 2 minutes and dehydrated by washing them in progressively higher concentrations of alcohol (70%-85%-100%) for 2 minutes each.

They are then air dried at room temperature.

The procedure is concluded by mounting the sample with DAPI counterstain and fitting the coverslip.

The p/v and/or v/v % concentrations of the components of the accelerating adjuvant additive according to the present invention on the slide are as follows:

To 5 µl of commercial molecular probe mix (containing on average 40% v/v formamide, 10% v/v dextran sulphate, 25% v/v others, 25% v/v H$_2$O) are added 5 µl of the accelerating adjuvant additive called DO (composed thus: 28.57% ethylene carbonate, 28.57% dextran sulphate, 28.57% H$_2$O, 14.29% SSC20×), giving a final mix on the slide containing 14% v/v ethylene carbonate, 19% v/v dextran sulphate and 26.05% v/v H$_2$O.

To 5 µl of commercial molecular probe mix (containing on average 40% v/v formamide, 10% v/v dextran sulphate, 25% v/v others, 25% v/v H$_2$O) are added 5 µl of the accelerating adjuvant additive called MO (composed thus: 1.07% NaOH, 49.46% dextran sulphate, 32.97% H$_2$O, 16.48% SSC20×), giving a final mix on the slide containing: 0.5% v/v NaOH, 29.7% dextran sulphate and 28.9% v/v H$_2$O.

To 5 µl of commercial molecular probe mix (containing on average 40% v/v formamide, 10% v/v dextran sulphate, 25% v/v others, 25% v/v H$_2$O) are added 5 µl of the accelerating adjuvant additive called DOMO (composed thus: 0.43% NaOH, 28.57% ethylene carbonate, 28.57% dextran sulphate, 28.57% H$_2$O, 13.86% SSC20×), giving a final mix on the slide containing: 14% ethylene carbonate, 0.2% v/v NaOH v/v, 19% v/v dextran sulphate and 26.05% v/v H$_2$O.

"Scoring" the Tissue Sections

The samples have been assessed both from a qualitative (signal intensity, percentage of nuclei with hybridization, background noise) and a quantitative point of view according to the guidelines for the various analyses:

Her-2: Wolff A. et al. (2013) 10.1200/JCO.2013.50.9984;

1p-19q: Smith, J. S., et al. (2000) J. Clin. Oncol. 18, 635-645;

ALK: NCCN Clinical Practice Guidelines in Oncology (NCCN GUIDELINES™). Non-Small Cell Lung Cancer (Version 3.2011). © 2011 National Comprehensive Cancer Network, Inc. Available at: NCCN.org. Accessed [Mar. 28, 2011].

3Q26, 8Q24, A-SAT CHR. 7: Riazimand S. H., Welkoborsky H.-J, Bernauer H. S, Jacob R, Mann W. J, Investigations for Fine Mapping of Amplifications in Chromosome 3q26.3.28 Frequently Occurring in Squamous Cell Carcinomas of the Head and Neck Oncology 2002; (63):385-392.

| Statistics relating to the lung | |
|---|---|
| Standard FISH | FISH according to the present invention |
| NEG | NEG |
| POS | POS |
| NEG | NEG |
| NEG | NEG |
| NEG | NEG |
| NEG | NEG |
| NEG | NEG |
| NEG | NEG |
| NEG | NEG |
| NEG | NEG |
| NEG | NEG |
| NEG | NEG |
| NEG | NEG |
| NEG | NEG |
| NEG | NEG |
| NEG | NEG |
| NEG | NEG |
| POS | POS |
| NEG | NEG |
| NEG | NEG |
| NEG | NEG |
| NEG | NEG |
| NEG | NEG |
| NEG | NEG |
| POS | POS |
| NEG | NEG |
| NEG | NEG |
| NEG | NEG |
| NEG | NEG |

| Dataset (Statistics relating to lung) | Standard FISH | FISH according to the present invention |
|---|---|---|
| Sample Size | 30 | 30 |
| Mean | 4.9033 | 4.5267 |
| Standard Deviation | 5.4397 | 6.1784 |
| T | 0.2506 | |
| degrees of freedom | 58 | |
| P (level of significance) | 0.8030 | |

| Statistics relating to the breast | | |
|---|---|---|
| ID | Standard FISH Interpretation of HER2 gene | FISH according to the present - invention Interpretation of HER2 gene |
| 1 | N* | N |
| 2 | N | N |
| 3 | N | N |
| 4 | A* | A |
| 5 | A | A |
| 6 | N | N |
| 7 | N | N |
| 8 | N | N |
| 9 | N | N |
| 10 | N | N |
| 11 | N | N |
| 12 | A | A |
| 13 | N | A |
| 14 | N | N |
| 15 | N | N |
| 16 | N | N |
| 17 | N | N |
| 18 | N | N |
| 19 | N | N |
| 20 | N | N |
| 21 | N | N |
| 22 | N | N |
| 23 | A | N |
| 24 | N | N |
| 25 | N | N |
| 26 | N | N |
| 27 | N | N |
| 28 | N | N |
| 29 | N | N |
| 30 | N | N |
| 31 | A | A |
| 32 | N | N |
| 33 | A | A |
| 34 | A | A |
| 35 | N | N |
| 36 | N | N |
| 37 | N | N |
| 38 | N | N |
| 39 | N | N |
| 40 | N | N |
| 41 | N | N |
| 42 | N | N |
| 43 | N | N |
| 44 | N | N |
| 45 | N | N |
| 46 | N | N |
| 47 | N | N |
| 48 | N | N |
| 49 | N | N |
| 50 | N | N |
| 51 | N | N |
| 52 | N | N |
| 53 | N | N |
| 54 | N | N |
| 55 | N | N |
| 56 | A | A |
| 57 | N | N |
| 58 | N | N |
| 59 | A | A |

*N: Indicates the cases that have no amplification of the HER2 gene
*A: Indicates the cases that have amplification

| FISH according to the present invention | Standard FISH | IQFISH ™* |
|---|---|---|
| 157-165 min (40 min of hybridization) | 2 days (12-20 hours of hybridization) | 210 min (60-120 min of hybridization) |

Concordance

| FISH according to the present invention Vs Standard FISH | 98% (range 96.8-99.1%) | <95% (range 92-99)* |
|---|---|---|

Statistics relating to breast
*Data from Her2 IQFISH ™ PHARM DX ™ Cod K5731 Second Edition, Dako Denmark, pages 21-22

The following Tables contain data on processing microscope images that show the comparison between the diameters of the signals in a sampling from each probe tested.

Signal diameter measurements - Brain 1p Deletion

| Nucleus | Method according to the present invention | | Standard method | |
|---|---|---|---|---|
| | Red | Green | Red | Green |
| 1 | 10 | 5.4 | 9.2 | 5.7 |
| 2 | 10 | 4 | 8.2 | 5.8 |
| 3 | 10 | 5.8 | 8.5 | 9.1 |
| 4 | 8 | 4 | 7.8 | 9 |
| 5 | 13 | 7.3 | 7.9 | 8.1 |
| 6 | 8 | 6.4 | 10.8 | 4 |
| 7 | 8.9 | 8.6 | 10.4 | 6.3 |
| 8 | 10 | 6.4 | 7.8 | 6.2 |
| 9 | 13 | 7.1 | 8.1 | 5.7 |
| 10 | 12.2 | 10.6 | 11 | 5.4 |
| Mean | 10.31 | 6.56 | 8.97 | 6.53 |

| | red vs red | green vs green |
|---|---|---|
| t | 1.8721 | 0.036343 |
| degrees of freedom | 18 | 18 |
| P (level of significance) | 0.07753305 | 0.971409 |
| Difference between the means observed | not significant for p < 0.01 | |

Measurement in pixels made on jpg image, 1376 × 1024 using GIMP 2.8 software

Signal diameter measurements - Brain 19q Deletion

| Nucleus | Method according to the present invention | | Standard Method | |
|---|---|---|---|---|
| | Red | Green | Red | Green |
| 1 | 7.2 | 5.1 | 8.5 | 7.6 |
| 2 | 5 | 6.8 | 8.9 | 8.5 |
| 3 | 5.8 | 6.7 | 4.2 | 7.2 |
| 4 | 6.3 | 5.7 | 4.1 | 4 |
| 5 | 5 | 5 | 5.8 | 4.5 |
| 6 | 4.5 | 5.8 | 6.7 | 4.2 |
| 7 | 5.4 | 8 | 9 | 5.7 |
| 8 | 7.2 | 5 | 5.1 | 4.1 |
| 9 | 7 | 7 | 7 | 10 |
| 10 | 7.1 | 4.1 | 7.3 | 8.1 |
| Mean | 6.05 | 5.92 | 6.66 | 6.39 |

Signal diameter measurements - Brain 19q Deletion

| | red vs red | green vs green |
|---|---|---|
| t | 0.9151 | 0.601527 |
| degrees of freedom | 18 | 18 |
| P (level of significance) | 0.372223 | 0.55499 |
| Difference between the means observed | not significant for p < 0.01 | |

Measurement in pixels made on jpg image, 1376 × 1024 using GIMP 2.8 software

Signal diameter measurements - Lung ALK

| Nucleus | Method according to the present invention | | Standard method | |
|---|---|---|---|---|
| | Red | Green | Red | Green |
| 1 | 8.6 | 7.3 | 10.4 | 7 |
| 2 | 8.5 | 6 | 9.4 | 6.5 |
| 3 | 6.2 | 7.6 | 8.1 | 6 |
| 4 | 9.1 | 5.1 | 7.1 | 7.4 |
| 5 | 9.2 | 7 | 8.2 | 8.1 |
| 6 | 7.8 | 6 | 7 | 5 |
| 7 | 7.8 | 8.1 | 6.3 | 7 |
| 8 | 11 | 7.1 | 8.2 | 6 |
| 9 | 7 | 8 | 5.8 | 5.1 |
| 10 | 7.8 | 5.1 | 6.4 | 8.5 |
| Mean | 8.3 | 6.73 | 7.69 | 6.66 |

| | red vs red | green vs green |
|---|---|---|
| t | 0.982835 | 0.1370 |
| degrees of freedom | 18 | 18 |
| P (level of significance) | 0.3387159 | 0.892526 |
| Difference between the means observed | not significant for p < 0.01 | |

Measurement in pixels made on jpg image, 1376 × 1024 using GIMP 2.8 ™ software

Measurements of signal diameters - Breast Her2

| Nucleus | Method according to the present invention | | Her 2 Standard method | |
|---|---|---|---|---|
| | Red | Green | Red | Green |
| 1 | 10.3 | 14 | 10.2 | 10.3 |
| 2 | 11.7 | 12 | 6.03 | 12.4 |
| 3 | 7.6 | 15 | 4.1 | 15.2 |
| 4 | 12 | 11 | 10 | 17 |
| 5 | 10.6 | 14 | 10.8 | 8 |
| 6 | 12.4 | 18.4 | 10.8 | 9.1 |
| 7 | 12.4 | 12.4 | 6.4 | 10.8 |
| 8 | 9.2 | 12 | 7.6 | 15.3 |
| 9 | 12.3 | 15.5 | 13.6 | 12.2 |
| 10 | 12.3 | 11.4 | 10.3 | 9.1 |
| Mean | 11.08 | 13.57 | 8.983 | 11.94 |

| | red vs red | green vs green |
|---|---|---|
| t | 2.0148 | 1.353512 |
| degrees of freedom | 18 | 18 |
| P (level of significance) | 0.05911328 | 0.192646 |
| Difference between the means observed | Not significant for p < 0.01 | |

Measurement in pixels made on jpg image, 1376 × 1024 using GIMP 2.8 software

Statistic of Carcinoma of oral cavity TERC 3Q26 (Thanks to rapid method, it is possible to efficiently hybridize obtaining surprising data on tissues from oral cavity).

| DYSPLASIA | RAPID FISH | STD FISH |
|---|---|---|
| Light | POS | FAILED |
| Light-Moderate | NEG | FAILED |
| Light | POS | FAILED |
| Light | POS | FAILED |
| No | POS | FAILED |
| Light | POS | FAILED |
| Moderate | POS | FAILED |
| Moderate | POS | FAILED |
| Moderate | POS | FAILED |
| No | POS | FAILED |
| Light | POS | FAILED |
| No | POS | FAILED |
| No | POS | FAILED |
| No | NEG | FAILED |
| No | NEG | FAILED |
| Light (low degree SIL) | NEG | FAILED |
| Light | NEG | FAILED |
| Light | NEG | FAILED |
| No | NEG | FAILED |
| No | NEG | FAILED |
| CA Microinvasive | POS | FAILED |
| No | NEG | FAILED |
| No | NOT TESTED | FAILED |
| Light | NOT TESTED | FAILED |
| No | NOT TESTED | FAILED |
| No | POS | FAILED |
| Light | POS | FAILED |

The invention claimed is:

1. A composition or a solution comprising a 1:1 mixture of:
   (a) an accelerating adjuvant additive solution for accelerating an in vitro nucleic acid hybridization, comprising either:
   (1)
   about 1.07% of NaOH,
   about 49.46% sodium dextran sulphate,
   about 32.97% $H_2O$, and
   about 16.48% SSC 20× citrate buffer; or
   (2)
   about 0.43% NaOH,
   about 28.57% sodium dextran sulphate,
   about 28.57% $H_2O$,
   about 13.86% SSC 20× citrate buffer;
   and about 28.57% ethylene carbonate; and
   (b) a molecular probe mix comprising about 40% v/v formamide, about 10% v/v sodium dextran sulphate, about 25% v/v others, and about 25% v/v $H_2O$.

2. The composition or solution of claim 1, wherein the accelerating adjuvant additive solution comprises:
   about 1.07% of sodium hydroxide,
   about 49.46% dextran sulphate,
   about 32.97% $H_2O$, and
   about 16.48% SSC 20× citrate buffer.

3. The composition or solution of claim 1, wherein the accelerating adjuvant additive solution comprises:
   about 0.43% sodium hydroxide,
   about 28.57% ethylene carbonate,
   about 28.57% dextran sulphate,
   about 28.57% $H_2O$, and
   about 13.86% SSC 20×.

4. The composition or solution of claim 1, having final concentrations comprising: about 14% ethylene carbonate, about 0.2% v/v NaOH, about 19% sodium dextran sulphate and about 26.05% v/v water.

5. A kit comprising the composition or solution of claim 1.

6. A slide comprising the composition of solution of claim 1.

7. A kit comprising:
   (a) an accelerating adjuvant additive solution for accelerating an in vitro nucleic acid hybridization, comprising either:
   (1)
   about 1.07% of NaOH,
   about 49.46% sodium dextran sulphate,
   about 32.97% $H_2O$, and
   about 16.48% SSC 20× citrate buffer; or
   (2)
   about 0.43% NaOH,
   about 28.57% sodium dextran sulphate,
   about 28.57% $H_2O$,
   about 13.86% SSC 20× citrate buffer;
   and about 28.57% ethylene carbonate; and
   (b) a molecular probe mix comprising about 40% v/v formamide, about 10% v/v sodium dextran sulphate, about 25% v/v others, and about 25% v/v $H_2O$.

8. A slide having disposed on a surface of the slide a solution comprising:
   (a) an accelerating adjuvant additive solution for accelerating an in vitro nucleic acid hybridization, comprising either:
   (1)
   about 1.07% of NaOH,
   about 49.46% sodium dextran sulphate,
   about 32.97% $H_2O$, and
   about 16.48% SSC 20× citrate buffer; or
   (2)
   about 0.43% NaOH,
   about 28.57% sodium dextran sulphate,
   about 28.57% $H_2O$,
   about 13.86% SSC 20× citrate buffer;
   and about 28.57% ethylene carbonate; and
   (b) a molecular probe mix comprising about 40% v/v formamide, about 10% v/v sodium dextran sulphate, about 25% v/v others, and about 25% v/v $H_2O$.

9. The slide of claim 8, the solution disposed on the slide has final concentrations comprising: about 14% ethylene carbonate, about 0.2% v/v NaOH, about 19% sodium dextran sulphate and about 26.05% v/v water.

* * * * *

UNITED STATES PATENT AND TRADEMARK OFFICE
CERTIFICATE OF CORRECTION

PATENT NO. : 11,021,739 B2
APPLICATION NO. : 15/549065
DATED : June 1, 2021
INVENTOR(S) : Enrico Di Oto, Valentina Monti and Sofia Asioli It is certified that error appears in the above-identified patent and that said Letters Patent is hereby corrected as shown below:

On the Title Page

Under Item (73) Assignee, please delete:
"ALMA MATER STUDIORUM UNEVERSETA DI BOLOGNA, Bologna (IT)"

And replace with:
"ALMA MATER STUDIORUM UNIVERSITA DI BOLOGNA, Bologna (IT)."

Signed and Sealed this
Twenty-ninth Day of June, 2021

Drew Hirshfeld
*Performing the Functions and Duties of the*
*Under Secretary of Commerce for Intellectual Property and*
*Director of the United States Patent and Trademark Office*